US008600690B2

(12) United States Patent
Ladebeck et al.

(10) Patent No.: US 8,600,690 B2
(45) Date of Patent: Dec. 3, 2013

(54) SYSTEM AND METHOD FOR THE TRANSMISSION OF SIGNALS

(75) Inventors: Ralf Ladebeck, Erlangen (DE); Markus Vester, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 809 days.

(21) Appl. No.: 12/585,373

(22) Filed: Sep. 14, 2009

(65) Prior Publication Data

US 2010/0074365 A1    Mar. 25, 2010

(30) Foreign Application Priority Data

Sep. 15, 2008  (DE) .......................... 10 2008 047 217

(51) Int. Cl.
*G01D 21/00* (2006.01)
*A61B 5/05* (2006.01)
*G01T 1/166* (2006.01)

(52) U.S. Cl.
USPC .... 702/85; 600/407; 250/363.03; 250/363.04

(58) Field of Classification Search
USPC .......................................................... 702/85
See application file for complete search history.

(56) References Cited

U.S. PATENT DOCUMENTS

| | | | |
|---|---|---|---|
| 6,115,409 A * | 9/2000 | Upadhyay et al. ............. | 375/144 |
| 2006/0029142 A1 * | 2/2006 | Arad .............................. | 375/260 |
| 2008/0027308 A1 * | 1/2008 | Ladebeck ..................... | 600/411 |

FOREIGN PATENT DOCUMENTS

| | | |
|---|---|---|
| DE | 10 2006 027 417 | 12/2007 |
| DE | 10 2006 027 417 A1 | 12/2007 |

OTHER PUBLICATIONS

German Office Action dated Jan. 15, 2010 for German Application No. 10 2008 047 217.4-35.
Bernard Widrow et al., "Adaptive Noise Cancelling: Principles and Applications", Proceedings of the IEEE, vol. 63, No. 12, Dec. 1975, p. 1692-1716.
Govind Kannan et al., "Equalizing Secondary Path Effects Using the Periodicity of fMRI Acoustic Noise", 30$^{th}$ Annual Int. IEEE EMBS Conference, Vancouver, British Columbia, Canada, Aug. 20-24, 2008, p. 25-28.

* cited by examiner

*Primary Examiner* — Sujoy Kundu
*Assistant Examiner* — Regis Betsch
(74) *Attorney, Agent, or Firm* — Harness, Dickey & Pierce, P.L.C.

(57) ABSTRACT

A method and a transmission system are disclosed for the transmission of wanted signals between a sensor and an evaluation unit. In order to suppress interference to the sensor signals due to external interference sources as far as possible, at least one embodiment of the inventive system has at least one signal receiver with the sensor for detecting a wanted signal and a signal processing device for conditioning the wanted signal, at whose output a mixed signal with a wanted signal component and an interference signal component from at least one interference source are present; an interference source signal input for detecting at least one interference source signal of the at least one interference source; a filter device for reconstructing the interference signal component as a function of the at least one interference source signal; and a subtractor for eliminating interference superimposed on the wanted signal.

10 Claims, 1 Drawing Sheet

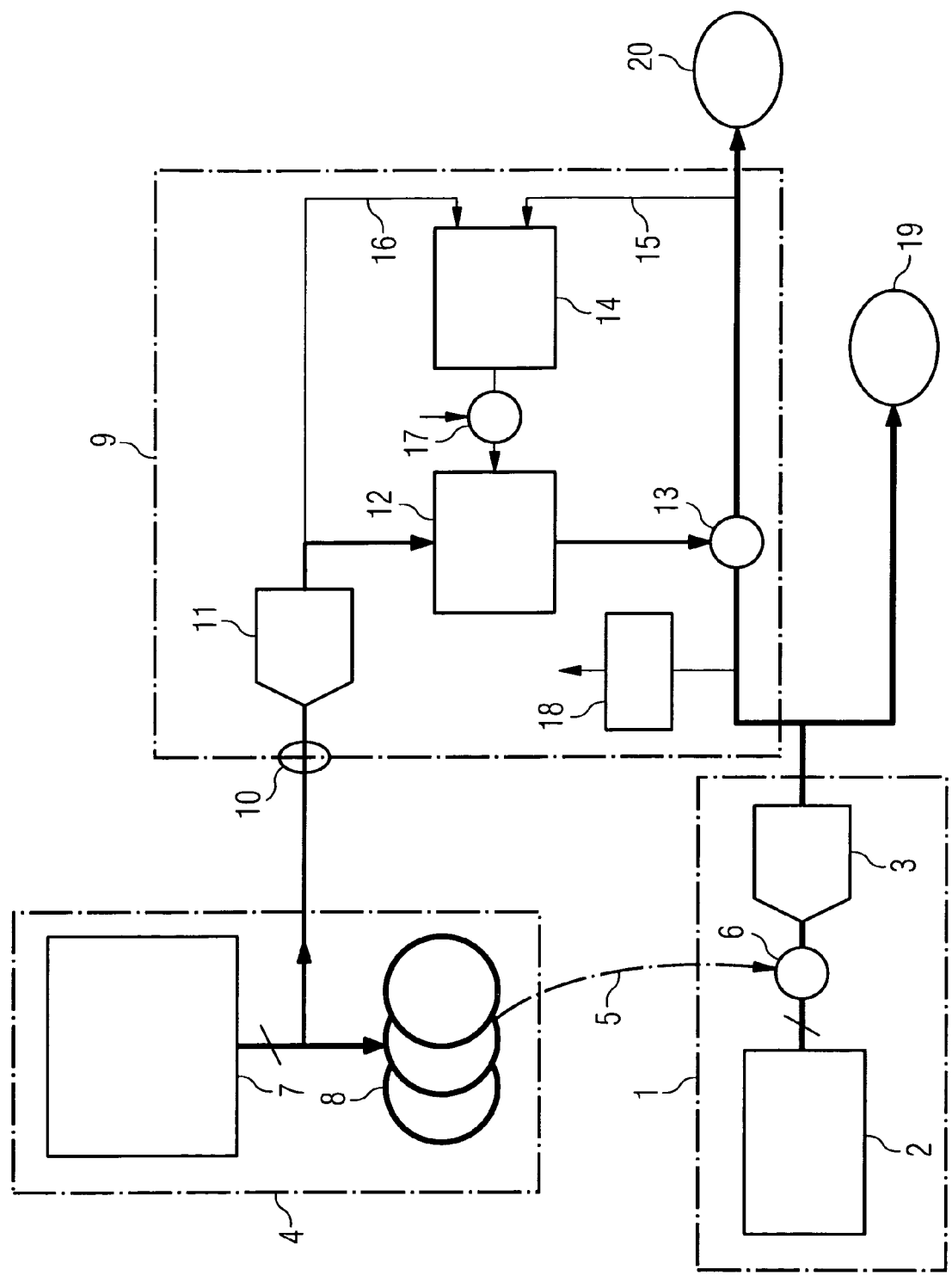

SYSTEM AND METHOD FOR THE TRANSMISSION OF SIGNALS

PRIORITY STATEMENT

The present application hereby claims priority under 35 U.S.C. §119 on German patent application number DE 10 2008 047 217.4 filed Sep. 15, 2008, the entire contents of which are hereby incorporated herein by reference.

FIELD

At least one embodiment of the invention generally relates to a system and/or method for the transmission of wanted signals between a sensor and an evaluation unit in the presence of at least one interference source.

In particular, at least one embodiment of the invention relates to the transmission of detector signals to a signal processing device in the presence of at least one interference source.

BACKGROUND

With a transmission of PET detector signals to the evaluation unit, when the positron emission tomography (PET) system is integrated into magnetic resonance (MR) tomography, the magnetic and electrical fields of the MR gradient system influence the analog signal processing electronics of the PET system and can induce interference signals, particularly at sensitive points (e.g. photodetectors and preamplifiers). In addition to the low-frequency gradient fields (frequency range 0 . . . 10 kHz) required for operation of the MR, there are often interference frequencies emanating from the gradient amplifier in the range of a few 100 kHz, which occur in the normally switched-mode operated power end stages and can often be adequately suppressed only with difficulty by filters in the gradient supply lines. The particular problem in this case is the spectral overlapping with the parts of the PET signal spectrum (under 5 MHz) which are necessary for a high accuracy when measuring the energy of the PET events. This energy resolution is important on the one hand for the qualification of pulse pairs compared with scattered quanta and on the other hand for the Anger method for lateral localization of the ionization within a scintillator block.

Therefore, the transmission of sensor signals with as little interference as possible is very important.

From DE 10 2006 027 417 A1, a sensor device is known which is particularly intended for a PET detector, which is operated in a magnetic field, which varies over time, of a magnetic resonance tomography system. It includes a sensor circuit for generating a sensor signal and an induction circuit in which a compensation signal is induced. These signals are combined in such a way that interference signals in the sensor signal, induced by the magnetic field which changes over time in the sensor circuit, are compensated for.

Design measures such as the minimization of the induction areas spanned by the signal lines or electrostatic screening can in fact reduce the interference signal injection. However a complete elimination of the injection is frequently not possible because of the difficult boundary conditions (e.g. temperature rise, vibration and secondary gradient fields due to eddy currents on screening surfaces).

SUMMARY

In at least one embodiment of the invention, interference to the sensor signals is suppressed due to external interference sources as far as possible.

According to at least one embodiment of the invention, those signals from an interference source which have a causative association with the interference signals are detected. This means that with an integrated MR-PET system, the gradient signals exciting the system are detected and the interference to the wanted signal is reconstructed from this. The reconstructed interference is then subtracted from the mixed signal with components of interference signals and components of PET (wanted) signals.

The inventive method, of at least one embodiment, for transmission of wanted signals between a sensor and an evaluation unit includes at least the following steps: detection of a wanted signal by a signal receiver with the sensor for detecting the wanted signal and a signal processing device for processing the wanted signal, with a mixed signal with a wanted signal component and an interference signal component from at least one interference source being present at an output of the signal receiver; detection of at least one interference source signal from the at least one interference source, reconstruction of the interference signal component as a function of the at least one interference source signal in a linear filter and subtraction of the reconstructed interference signal component from the mixed signal in order to recover the wanted signal component.

Example embodiments of the inventive method include the following, as a further feature or a combination of further features, so that:
  reconstruction of the interference signal component takes place by folding with an impulse response which is a filter transmission function when Fourier-transformed;
  the filter transmission function is determined by calibration of the system;
  for calibration, M various excitation patterns are generated in turn with the at least one interference source and are recorded in parallel for each of the N sensors;
  several excitation models are averaged for calibration;
  uncorrelated signals, especially signals from a background activity of the sensor which are uncorrelated with gradient signals are masked during calibration;
  determination of the filter transmission function takes place adaptively or said filter transmission function is adaptively improved;
  the adaptive determination takes place in a predetermined time window;
  the mixed signal and the interference source signal are digitized and the filtering takes place by means of digital signal processing;
  high-frequency signal parts of the wanted signal component are used for discrimination of the interference signal component;
  the detection of a mixed signal and the detection of the at least one interference source signal on the one hand and the reconstruction of the interference signal component and filtering of the mixed signal on the other hand take place with a time lag;
  the sampling rate chosen for the interference source signal is lower than the sampling rate for the mixed signal, if the interference signal component is only in the lower frequency range;
  filtering takes place using FFT algorithms;
  the wanted signal component includes a PET detector signal and the at least one interference source is a gradient coil system in an MRI magnet, with the interference source signal including a control signal for a gradient coil system.

The inventive transmission system, of at least one embodiment, for transmission of wanted signals between a sensor and an evaluation unit includes: at least one signal receiver with the sensor for detecting a wanted signal and a signal processing device for processing the wanted signal, at whose output a mixed signal with a useful signal component and an interference signal component from at least one interference source are present, an interference source signal input for detecting at least one interference source signal from the at least one interference source, a filter for reconstructing the interference signal component relative to the at least one interference source signal and a subtractor for subtracting the reconstructed interference signal component from the mixed signal in order to recover the wanted signal component.

Example embodiments of the inventive transmission system have the following, as a further feature or combination of further features, so that:

- the filter uses an impulse response or a filter transmission function when reconstructing the interference signal component from the mixed signal;
- a memory is provided for storing the impulse response or filter transmission function which is determined during a calibration of the system;
- in the memory, M various excitation models, which are generated with M interference sources and recorded in parallel for each of the N sensors, can be stored in turn;
- an average value device is provided for forming average values from several similar excitation models;
- a discriminator is provided for discriminating uncorrelated signals from the interference signal component;
- a control circuit is provided for the adaptive determination or improvement of the impulse response or transmission function;
- a time discriminator is provided for adaptive reconstruction in a predetermined time window;
- AD converters are provided for digitizing the mixed signal and the interference source signal, and digital signal processing is used for filtering;
- a frequency discriminator is provided for discriminating high-frequency signal parts of the wanted signal component from the interference signal component;
- a buffer store is provided for storing and outputting the mixed signal and the at least one interference source signal, so that the detection of the mixed signal and of the interference source signal on the one hand and the reconstruction of the interference signal component and the filtering of the mixed signal on the other hand can be carried out with a time lag;
- the AD converter for the interference signal operates with a lower sampling rate than the AD converter for the mixed signal, if the interference signal component is only in the lower frequency range;
- an FFT algorithm is implemented in the filter;
- the sensor has a PET detector and the at least one interference source is a gradient coil system in an MRI magnet, with the interference source signal having a control signal for a gradient coil system.

At least one embodiment of the invention has an advantage that effective compensation for interference influences in an integrated PET-MRI unit can be implemented at comparatively low cost in material and sometimes older units can also be retrofitted.

BRIEF DESCRIPTION OF THE DRAWINGS

Further features and advantages of the invention result in the following description of example embodiments, with reference being made to the accompanying drawing by using a FIGURE.

The figure shows a block diagram of an embodiment of the inventive transmission system.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Using FIG. 1, the principle of the inventive transmission system of an embodiment is explained in the following. With the transmission system, a measurement signal from a signal receiver 1 is forwarded to an evaluation unit. For this purpose, the signal receiver 1 has a sensor 2, which in particular can be a detector for radioactive radiation. Depending on the application of an embodiment of the invention, an antenna can also in principle be used as a sensor. Because the output signals from detectors are usually very weak, the signals must be preamplified and/or digitized directly at the detector output. For this purpose, the signal receiver 1 has a processing device 3, such as an AD converter, for the detector signals.

Although the lines between the sensor 2 and the AD converter 3 are kept as short as possible the interspersion of electromagnetic interference signals into the signal receiving electronic system is unavoidable. These interference signals originate from an interference source 4 in the vicinity of the signal receiver 1 and usually cannot be fully screened. From the interference source 4, which in particular can be a switched-mode magnetic coil system, an electromagnetic interference signal 5 is transmitted to the signal receiver 1 and there it is injected into the conditioning unit. This is shown symbolically as injection point 6 within the signal receiver 1.

The electromagnetic interference signals 5 originate at gradient coils 8, especially from preamplifiers 7, with which they are controlled. The preamplifier end stages, which are often operated using pulse-width modulation, use pulses with steep edges and therefore with strong harmonics. Although the spectra for control of the gradient coils 8 is in the frequency range of up to 10 kHz, high-frequency parts of the control pulses up to the MHz range still contribute to the interference signals. The high-frequency parts 5 are captured in the signal receiver 1 and are again present, together with the actual wanted signal, at the output of the signal receiver 1.

In addition to direct electromagnetic coupling, the gradient coil signals can also indirectly cause interspersion into the signal processing due to vibrations. Due to Lorenz forces, the gradient coils experience movements which are transmitted to the signal-carrying conductors of the PET detector either mechanically or acoustically. Their vibration in the strong magnetic basic field in turn induces interfering voltages. These are also linked to the gradient currents by a linear transmission function and can be eliminated without further measures by an embodiment of the inventive method or by an embodiment of the inventive transmission system.

To eliminate the interference signals correlated with the switching rates of the gradient coils from the mixed signal of the signal receiver 1 and isolate the actual wanted signal of the sensor 2, an interference source signal of the interference source 4, which is correlated with the interference signal, is imported by a compensation unit 9 via one of its inputs 10. This interference source signal is conditioned in the compensation unit 9 directly after the input 10 in a corresponding switching circuit 11, such as an AD converter, for the further evaluation in the unit 9.

The conditioned interference source signal is imported by a filter device 12 in order to output a reconstructed interference signal which is as equal as possible to the injected interference signal. The purpose of this reconstructed interference signal component is to compensate for the corresponding actual interference signal component in the output signal of the signal receiver 1. The elimination of the interference signal component from the mixed signal coming from the signal receiver 1 with wanted signal component and interference signal component takes place in a subtractor 13. Furthermore in this subtractor 13, the mixed signal from the signal receiver 1 in particular can be superimposed by the reconstructed interference signal component (with a reversed sign). The interference part in the mixed signal is thus theoretically eliminated.

When eliminating the interference signal component in the mixed signal from the signal receiver 1 by subtraction of the reconstructed value for the interference, it is assumed that the analog system is operated in the linear range and no overmodulation which could result in non-linear behavior, is caused by the interference. The system consisting of gradient coils and PET receivers can then be considered a linear filter with M inputs and N outputs. The transmission function of the system can be represented in the frequency range by a frequency-related M×N matrix H (f). An equivalent representation in the time range includes N×M input responses. The M inputs are, for example, occupied by the three gradient axes or by the six supply lines of the gradient coils, even if common mode or push-pull demodulation interference components, each of which is partially independent of the other, are to be eliminated. The evaluated PET channels are registered at the N outputs, if necessary after some of them have already been combined. The number of outputs can, for example, be 200. For this purpose, the system must have a corresponding number of memories (not illustrated) for storing the calibration measurement(s) of the system.

The matrix of the transmission functions H (f) is essentially static and can be uniquely determined by a set of calibration measurements. To do this, M various excitation models (e.g. a pulse or chirp on each axis) must be generated in succession by the gradient system and the responses to each injected into the N channels recorded in parallel. To improve the signal-noise ratio during the calibration, an averaging of several excitations is preferably carried out. For this purpose, the system had an averaging device (not illustrated), in order to form average values from several excitation models.

During calibration it is possible that the calibration is disturbed by undesirable spontaneous radioactive events. This could be the case with or without a PET emitter and is due to residual or background activity of the detector material. Because these spontaneous events are, however, uncorrelated with the gradient signals, they can be well suppressed by averaging. For this purpose, a discriminator (not illustrated), which eliminates the uncorrelated signals from the interference signal component, is provided in the system. Furthermore, these pulses can be easily detected in advance because of their steep edges, and sampled values in their neighboring time domain can be precluded from the averaging. The system is equipped with a time discriminator (not illustrated) for this purpose.

With the signal "corrected" in this way, a triggering 18 is carried out in order to be able to assign a precise event time-point to the signal. In accordance with the normal function of a PET, the signal is furthermore compared in a coincidence evaluation 19 with a second signal in order to check whether both signals can be traced back to the same radioactive decay. The "corrected" signal is also subjected to an energy and location evaluation 20 in order to identify the point of origin of the radioactive decay.

The embodiment of the compensation unit 9 shown in FIG. 1 not only enables a one-off calibration but also an adaptive matching of the filter used for the reconstruction of the interference signal. An adaptive filtering enables advanced correction of the measuring signal. For this purpose, a correlation of each of the interference-suppressed PET output signals with each of the exciting gradients is performed during the ongoing measurement and the correlation results are used for a gradual improvement in the transmission functions. In this case also, the adaptation with respect to received PET pulses and in time periods with a low gradient activity can be masked. By means of the adaptation, the remaining gradient interference is suppressed to zero with almost any degree of accuracy, even if the geometry of the system has gradually changed, e.g. due to heating.

The signal corrected in the subtractor 13 is individually compared in a correlator 14 with the interference source signal from the interference source signal conditioning 11. The corrected signal is fed via a feedback line 15 to the correlator 14 and the interference source input signal is also fed via an interference source signal tap 16 to the correlator 14. The output of the correlator supplies the correlation result, which represents a time function with which the impulse response used in the filter up until then is improved. In an ideal case, the signals on both lines are the same and the correlation result 14 is zero, i.e. a change in the impulse response of the filter 12 is not necessary. Otherwise, where there is a deviation of the signal on the feedback line 15 from the interference source signal on the interference source signal tap line 16, the impulse response of the filter 12 is adapted so that the signal on the feedback line 15 and the interference source signal on the line 16 have the minimum possible correlated amounts. This automatic tracking of the impulse response (or of the transmission function corresponding to this) for the filter 12 can be activated or deactivated by a suitable adaption enable device 17, i.e. in particular the reconstruction of the interference signal component can be limited to a predetermined time frame. For this purpose, a time discriminator (not illustrated), with which the predetermined time window is opened or closed for adaptation, is provided in the system.

With all the above named types of interference elimination, the mixed signal and the interference source signal are preferably digitized and the filtering takes place by means of digital signal processing. Because modern forms of PET signal processing already detect each of the N channels by means of an AD converter, only the, e.g. six, AD converters 11 need to be added for the control signals of the gradient coils 8. Furthermore, it is necessary in digital signal processing to allow M filters to run for each of the N channels. By way of the digitization of the evaluation and filtering, a maximum flexibility of the filtering and the possibility of their adaptation to changed framework conditions is guaranteed. This, for example, enables FFT algorithms for filtering the mixed signal to be simply implemented. By use of fenestrated Fast-Fourier transformations (FFT) for filtering in the frequency range, the computing expense can be reduced compared to a direct folding in the time range. The same also applies for correlation for the adaptation of the filter.

With digital processing of the data, the sampling rate of the respective signals can also be chosen as required. Thus, the sampling rate chosen for the interference source signal at input 10 can be selected as lower than the sampling rate for the mixed signal from the signal receiver 1, if the interference source signal or the interference signal component is only in the lower frequency range. Furthermore, high-frequency signal parts of the wanted signal component can be utilized for discriminating the interference signal component. The filtering out of these high-frequency parts takes place by means of a high-pass filter (not illustrated).

Also, because of the unlimited copying capability of digital data, the mixed signal and the interference source signal on the one hand and the reconstruction of the interference signal component and subtraction from the mixed signal on the other hand can be carried out with a time lag. This makes "offline" processing possible, which means that signal correction does not have to take place in real time but instead the gradient channels can be recorded parallel to the PET channels and the corrections carried out a posteriori before the image reconstruction. For this purpose, the system has a buffer memory (not illustrated), in which the mixed signal and the interference source signal can be stored and read, so that the detection of the mixed signal and of the interference source signal on the one hand and the reconstruction of the interference signal component and the filtering of the mixed signal on the other hand can be carried out after a time lag.

The inventive method of an embodiment is thus particularly suitable for application with MR-PET devices, with which the wanted signal component includes a PET detector signal and the interference source is an MRI magnet, with the interference source signal being used as a control signal for a gradient coil system.

The method can be further optimized for use with MR-PET recording. For instance, calculation of the filtered signals can be limited to the time domain of detected PET coincidence pairs. In practice, it is often possible also to detect PET coincidences in the presence of low-frequency gradient interference by using the high-frequency signal components present in the steep edges. It is then sufficient for the determination of pulse energies to calculate the filtered radiating signals for only a few samples in the environment of the events. It is thus possible, particularly in scenarios with low radioactivity, to reduce to a large extent the computing and storage cost.

The sampling rate chosen for the gradient signal can be lower than that for the mixed signal. Because the interference spectra generated by the gradient coils is usually only in the low frequency range, they do not have to be sampled with the full sampling rate of the PET system. A lower sampling rate (e.g. 2 MHz) can also be chosen for the AD converter 11 of the gradient signal and can be interpolated later to a denser sampling rate (e.g. 20 MHz) for determining the energy of the PET events. The computing costs for filtering and for offline correction also memory space can thus be saved.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for transmitting wanted signals between a sensor and an evaluation unit of a PET detector, the method comprising:
    detecting a wanted signal by a signal receiver with the sensor for detecting the wanted signal and a signal processing device for conditioning the wanted signal, with a mixed signal with a wanted signal component and an interference signal component from a gradient coil system of a MRI magnet acting as at least one interference source being present at an output of the signal receiver, wherein the wanted signal component includes a PET detector signal;
    importing at least one interference source signal of the at least one interference source from a preamplifier of the interference source, the interference source signal being a set of control signals for controlling switching of the gradient coil system; and
    reconstructing the interference signal component as a function of the imported at least one interference source signal in a linear filter with a filter transmission function and subtracting the reconstructed interference signal component from the mixed signal in order to recover the wanted signal component.

2. The method as claimed in claim 1, wherein the filter transmission function is determined by calibration of the system.

3. The method as claimed in claim 2, wherein a plurality of various excitation models are generated in turn with the at least one interference source for calibration and are recorded in parallel for each of a plurality of sensors.

4. The method as claimed in claim 3, wherein several excitation models are averaged for calibration.

5. The method as claimed in claim 3, wherein uncorrelated signals, including signals from a background activity of the sensor uncorrelated with gradient signals, are masked during calibration.

6. The method as claimed in claim 2, wherein uncorrelated signals are masked during calibration.

7. The method as claimed in claim 6, wherein the uncorrelated signals are signals from a background activity of the sensor uncorrelated with gradient signals.

8. The method as claimed in claim 1, wherein the mixed signal and the interference source signal are digitized and filtering taking place using digital signal processing.

9. The method as claimed in claim 1, wherein the detection of a mixed signal and the detection of the at least one interference signal, and the reconstruction of the interference signal component and the filtering of the mixed signal, are carried out with a time lag.

10. The method as claimed in claim 1, wherein the filtering takes place using FFT algorithms.

* * * * *